United States Patent

Munch et al.

Patent Number: 5,298,122
Date of Patent: Mar. 29, 1994

[54] MEASURING DEVICE AND METHOD FOR MEASURING THE CROSSWISE PROFILE OF A PAPER WEB

[75] Inventors: Rudolf Munch, Ravensburg; Elmer Weisshuhn, Vogt, both of Fed. Rep. of Germany

[73] Assignee: Sulzer Escher Wyss, Ravensburg, Fed. Rep. of Germany

[21] Appl. No.: 646,619

[22] PCT Filed: Aug. 1, 1989

[86] PCT No.: PCT/DE89/00499
§ 371 Date: Jan. 29, 1991
§ 102(e) Date: Jan. 29, 1991

[87] PCT Pub. No.: WO90/01673
PCT Pub. Date: Feb. 22, 1990

[30] Foreign Application Priority Data

Aug. 10, 1988 [DE] Fed. Rep. of Germany ....... 3827084

[51] Int. Cl.$^5$ ................................................ D21F 1/06
[52] U.S. Cl. .................................... 162/259; 162/263; 162/11; 364/471
[58] Field of Search ............... 162/DIG. 11, 263, 259, 162/DIG. 10; 364/471, 563

[56] References Cited

U.S. PATENT DOCUMENTS

| | | |
|---|---|---|
| 3,108,844 | 10/1963 | Alexander et al. |
| 3,557,351 | 1/1971 | Doering ................. 364/469 |
| 3,609,318 | 9/1971 | Anderson ............ 162/DIG. 11 |
| 4,271,699 | 6/1981 | Williamson ............. 73/159 |
| 4,874,467 | 10/1989 | Karlsson ............... 162/259 |
| 4,939,929 | 7/1990 | Ostman ................. 364/471 |

FOREIGN PATENT DOCUMENTS

| | | |
|---|---|---|
| 2005655 | 9/1970 | Fed. Rep. of Germany. |
| 3148800 | 6/1983 | Fed. Rep. of Germany. |
| 60-177202 | 9/1985 | Japan. |
| 60-177203 | 9/1985 | Japan. |
| 60-177204 | 9/1985 | Japan. |
| 1228001 | 4/1971 | United Kingdom. |

OTHER PUBLICATIONS

English Abstract of Japanese Application Nos. 60-177202, 60-177203, and 60-177204.
Offer Proposal to Paul Reitemeyer, Jun. 4, 1987.
Operating Instructions about KDM-up machine, pp. 34, 35 and 36.
Description of Berger Lahr GmbH machine KIP 500, Jun. 1987, pp. 1 to 26.

Primary Examiner—W. Gary Jones
Assistant Examiner—Brenda A. Lamb
Attorney, Agent, or Firm—Sandler Greenblum & Bernstein

[57] ABSTRACT

A measuring bridge, fixed in place above a moving paper web and disposed crosswise to it, is provided, having a measuring head, movable back and forth—crosswise to the paper web—, for determining the measuring values for judging the thickness of the paper web at the measuring spots or point on top of which the measuring head happens to be. The measuring device, has a process management system, in which a traversing flow program has been installed, in accordance with which the traversing time and/or the reversing time of the measuring head are changed after each traverse of the measuring bridge. Because of this, the frequency of the measurements along the web becomes irregular. This prevents false evaluations of the cross section and, as a consequence, inappropriate control instructions of a control computer.

7 Claims, 1 Drawing Sheet

MEASURING DEVICE AND METHOD FOR MEASURING THE CROSSWISE PROFILE OF A PAPER WEB

BACKGROUND OF THE INVENTION

The present invention relates to a measuring device and method for measuring the crosswise profile of a paper web.

Up to now it has been customary to move the measuring head along the measuring bridge, crosswise to the paper web, with always the same speed. This results in the measurements always taking place in the same time frame at the individual measurement places.

The goal of measuring is to determine the stable cross section of the web and to make corrections to the accumulation of material accordingly, for example by the required adjustment of the inside width of the headbox gap or slice —and along and crosswise to the direction of running—in order to achieve a desired cross section or transverse profile of the web. Formation of the desired cross section of the web is impaired by interference or disturbances in the material flow from the headbox. These interferences, which may result in deviations from the desired cross section, cannot always be precisely determined. It may happen that the frequency of the interference or disturbance and the frequency of measurement are in a whole number relationship to each other. In this case the measurement result may falsely indicate a deviation from the desired cross section. Therefore, a correction as a result of such a measurement cannot lead to the attainment of the desired cross section or transverse profile of the web.

GB-A-1 218 001 discloses a measuring device for determining average values, for example, for the thickness of a passing web. In this connection the sensing speed is controlled proportionally to the speed of movement of the web. However, this measuring system is not capable of preventing the falsification of the results caused by the matching of the measuring frequency and the interference frequency.

SUMMARY OF THE INVENTION

It is the object of the invention to suggest a device and a method for measuring the cross section of the paper web for the purpose of determining the stable cross section over a considered length of the paper web. This is intended to prevent miscalculations of the cross section and, consequently, inappropriate adjustment actions by means of the control devices affecting the cross section of the paper web.

Now in order to implement these and still further objects of the present invention, which will become more readily apparent as the description proceeds, the measuring device for measuring the crosswise profile or cross-section of a paper web, of the present development is manifested, among other things, by the features that there is provided a stationarily arranged measuring bridge extending in transverse direction of the paper web and beneath or in cooperative relationship with which there is movable the paper web in a predetermined direction of travel. A measuring head is provided for the measuring bridge and is movable back and forth on the measuring bridge in the transverse direction of the paper web at a measuring frequency for determining a measuring value representative of the thickness of the paper web at a predetermined measuring location above which there is momentarily located the measuring head during movement of the measuring head back and forth on the measuring bridge. The measuring bridge has measuring points or spots located along the measuring bridge and at respective locations of the measuring points the measuring head determines respective measuring values representative of the thickness of the paper web at predetermined measuring locations in the transverse direction of the paper web. Further, there are provided means for altering the measuring frequency of the measuring head which comprise process management means provided with traversing flow program means for selectively changing at lest any one of (i) a traversing time of the measuring head in the transverse direction of the paper web and (ii) a waiting time of the measuring head between two transverse passes of the measuring head in the transverse direction of the paper web. As a result, determination of the measuring values along the moving paper web at each individual measuring point is performed with continuously changing time intervals, whereby errors in measurement of the cross section of the paper web arising due to coincidence of the measuring frequency with a disturbance frequency in the formation of the paper web is substantially avoided due to changes in the measuring frequency of the measuring head.

Regarding the inventive method of measuring the cross section of a paper web forming downstream of a headbox, such comprises moving a paper web in a predetermined direction of travel in cooperative relationship past a stationarily arranged measuring bridge extending in transverse direction of the paper web. Then a measuring head provided for the measuring bridge is moved back and forth on the measuring bridge past measuring points located along the measuring bridge in transverse direction of the paper web at a measuring frequency for determining at respective locations of the measuring points respective measuring values representative of the thickness of the paper web at the predetermined measuring locations in the transverse direction of the paper web. There is produced by means of the measuring head measuring values representative of the thickness of the paper web at predetermined measuring locations in the transverse direction of the paper web during movement of the measuring head back and forth on the measuring bridge. Furthermore, there is altered the measuring frequency of the measuring head for selectively changing at least any on of (i) a traversing time of the measuring head in the transverse direction of the paper web and (ii) a waiting time of the measuring head between two transverse passes of the measuring head in the transverse direction of the paper web, so that determination of the measuring values along the moving paper web at each individual measuring point is performed with continuously changing time intervals, whereby errors in measurement of the cross section of the paper web arising due to coincidence of the measuring frequency with a disturbance frequency in the formation of the paper web is substantially avoided due to changes in the measuring frequency of the measuring head.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
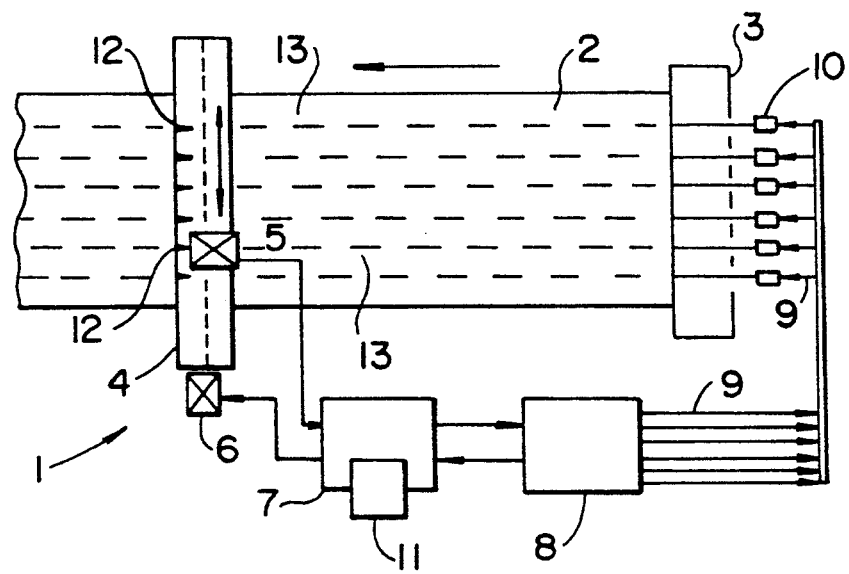
FIG. 1 is a schematic view of an exemplary embodiment of measuring device constructed according to the present invention in a top plan view.

The measuring device 1 for measuring the cross section of a web of material, in this case a paper web 2, formed downstream of the headbox 3 and moving at a given speed in the direction of the depicted arrow, has a measuring bridge 4, which is disposed fixed in place over the web 2 and crosswise to it. A measuring head 5 is disposed on the measuring bridge 4, which can be moved back and forth along the measuring bridge 4, i.e. crosswise in relation to the web 2 moving under the measuring bridge. This movement is generated by a reversible drive motor 6, the rpm of which are are adjustable. The motor 6 is controlled by a process management system 7 which, for evaluating the cross section, is also supplied with the measured values detected at the measurement markers or spots or points 12.

The individual measurements are each taken alone imaginary lines 13 of the paper web 2, which extend below the individual measuring markers or spots or points 12 along the web.

A traversing flow program 11 has been installed in the process management system 7, in accordance with which the drive motor 6 is controlled. This is accomplished in such a way, that the traversing speed of the measuring head 5 is changed after each traversal of the paper web 3, or that the length of the waiting period between two traverses is changed. It is also possible to change the traversing speed as well as the length of the waiting period continuously. The goal of the measuring method is to perform the measurements along each individual line 13 at irregular intervals, which are different from each other.

Figure 2:
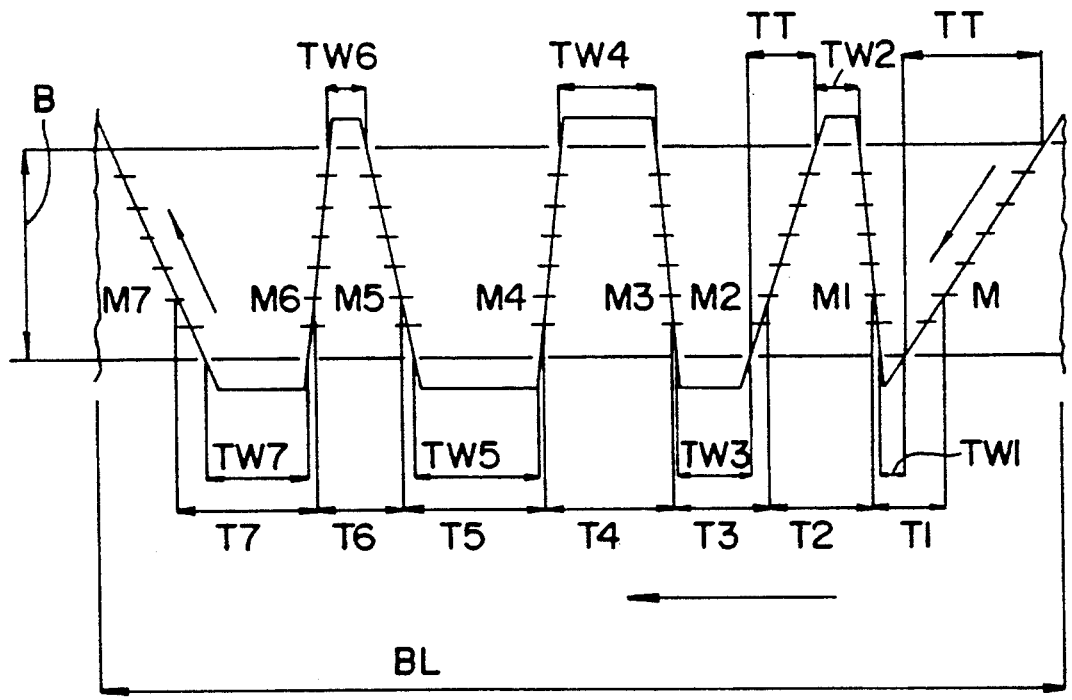
FIG. 2 is an illustration of the measuring method with the aid of the measuring device in accordance with the invention.

An example of such an action is schematically illustrated in FIG. 2.

The sequence of measurements is shown with respect to a longitudinal section BL of the paper web 2 of a width B. The paper web moves in the direction of the depicted arrow. The completed or full line across the web 2 represents the movement of the measuring head 5 in relation to the paper web 2, taking place with irregular traversing speeds. The traversing time of the measuring head 5 during the first two passes is indicated by TT. The individual measuring points along one of the lines 13 have been designated by M to M7 and are indicated by a line in the longitudinal direction. The distance between the individual traversing lines is given by the length of the respective waiting times TW1 to TW7 and indicates the time elapsing or being planned to elapse between two successive traverses. The distances between two successive measurements M to M7 are indicated by T1 to T7 and are different from each other, so that the measurements were taken with a changing measuring frequency. Since this frequency was preset and changed completely arbitrarily, there is no practical likelihood that this frequency could coincide with the frequency of an interference in the web formation, which would lead to falsification or misreading of the measurement. The possibility of a false reading of a stable cross-sectional deviation has been eliminated by the irregularity of the measurement.

The readjustment of the material gap of the headbox 3 following the statistical evaluation of the measurements can be advantageously performed by means of a control computer 8. Its control instructions are supplied via lines 9 to the adjustment elements 10, which have been provided for adjusting the inside width of the headbox gap crosswise to the web 2. It is conceivable that the control instructions of the control computer 8 are also supplied to other control devices for affecting the cross section of the paper web. Adjustment devices upstream as well as downstream of the web forming zone of the paper-making machine can be controlled.

While there are shown and described present preferred embodiments of the invention, it is distinctly to be understood the invention is not limited thereto, but may be otherwise variously embodied and practiced within the scope of the following claims.

We claim:

1. A measuring device for measuring the cross section of a paper web forming downstream of a headbox, comprising:

a stationarily arranged measuring bridge extending in transverse direction of the paper web and in cooperative relationship with which there is movable the paper web in a predetermined direction of travel;

a measuring head provided for the measuring bridge and movable back and forth at the measuring bridge in the traverse direction of the paper web at a measuring frequency for determining a measuring value representative of the thickness of the paper web at a predetermined measuring location where there is momentarily located the measuring head during movement of the measuring head back and forth at the measuring bridge;

the measuring bridge having measuring points located along the measuring bridge and at respective locations of the measuring points the measuring head determines respective measuring values representative of the thickness of the paper web at predetermined measuring locations int he transverse direction of the paper web;

means for altering the measuring frequency of the measuring head independent of the speed of travel of the paper web; and the altering means comprising process management means provided with traversing flow program means for selectively changing, independent of the speed of travel of the paper web, at least any one of (i) a traversing time of the measuring head in the transverse direction of the paper web and (ii) a waiting time of the measuring head between two transverse passes of the measuring head in the transverse direction of the paper web, so that determination of the measuring values along the moving paper web at each individual measuring point is performed with continuously changing time intervals, whereby errors in measurement of the cross section of the paper web arising due to coincidence of the measuring frequency with a disturbance frequency in the formation of the paper web is substantially avoided due to changes in the measuring frequency of the measuring head.

2. A method of measuring the cross section of a paper web forming downstream of a headbox, comprising the steps of:

moving a paper web in a predetermined direction of travel in cooperative relationship past a stationarily arranged measuring bridge extending in transverse direction of the paper web;

moving a measuring head provided for the measuring bridge back and forth at the measuring bridge past measuring points located along the measuring bridge in transverse direction of the paper web at a measuring frequency for determining at respective locations of the measuring points respective measuring values representative of the thickness of the paper web at the predetermined measuring locations in the transverse direction of the paper web;

producing by means of the measuring head measuring values representative of the thickness of the paper web at predetermined measuring locations in the transverse direction of the paper web during movement of the measuring head back and forth at the measuring bridge; and altering the measuring frequency of the measuring head for selectively changing at least any one of (i) a traversing time of the measuring head in the transverse direction of the paper web and (ii) a waiting time of the measuring head between two transverse passes of the measuring head in the transverse direction of the paper web, so that determination of the measuring values along the moving paper web at each individual measuring point is performed with continuously changing time intervals, whereby errors in measurement of the cross section of the paper web arising due to coincidence of the measuring frequency with a disturbance frequency in the formation of the paper web is substantially avoided due to changes in the measuring frequency of the measuring head.

3. The method of measuring the cross section of a paper web according to the claim 2, wherein:

the step of altering the measuring frequency of the measuring head entails changing both (i) the traversing time of the measuring head in the transverse direction of the paper web and (ii) the waiting time of the measuring head between two transverse passes of the measuring head in the transverse direction of the paper web.

4. The method of measuring the cross section of a paper web according to claim 2, wherein:

the step of altering the measuring frequency of the measuring head entails changing the measuring frequency for each transverse pass of the measuring head in the transverse direction of the paper web.

5. The method of measuring the cross section of a paper web according to claim 2, further including the steps of:

determining the cross-sectional profile of the paper web throughout a predetermined length of the paper web as a function of the measuring values; and adjusting the cross section of the paper web upon deviation of the determined cross-sectional profile of the paper web from a predetermined desired value.

6. The method of measuring the cross section of a paper web according to claim 5, wherein:

the step of adjusting the cross section of the paper web upon deviation of the determined cross-sectional profile of the paper web from a predetermined desired value entails controlling an inner width of an outlet slice of the headbox.

7. A method of measuring the cross section of a paper web forming downstream of a headbox, comprising the steps of:

moving a paper web in a predetermined direction of travel in cooperative relationship past a stationarily arranged measuring bridge extending in transverse direction of the paper web;

moving a measuring head provided for the measuring bridge back and forth at the measuring bridge past measuring points located along the measuring bridge in transverse direction of the paper web at a predetermined measuring frequency for determining at respective locations of the measuring points respective measuring values representative of the thickness of the paper web at predetermined measuring locations in the transverse direction of the paper web;

producing by means of the measuring head measuring values representative of the thickness of the paper web at predetermined measuring locations in the transverse direction of the paper web during movement of the measuring head back and forth at the measuring bridge; and altering the measuring frequency of the measuring head, independent of the speed of travel of the paper web, for selectively changing at least any one of (i) a traversing time of the measuring head in the transverse direction of the paper web and (ii) a waiting time of the measuring head between two transverse passes of the measuring head in the transverse direction of the paper web, so that determination of the measuring values along the moving paper web at each individual measuring point is performed with continuously changing time intervals, whereby errors in measurement of the cross section of the paper web arising due to coincidence of the measuring frequency with a disturbance frequency in the formation of the paper web is substantially avoided due to changes in the measuring frequency of the measuring head.

* * * * *